(12) United States Patent
Tyler et al.

(10) Patent No.: US 9,421,366 B2
(45) Date of Patent: Aug. 23, 2016

(54) METHODS OF TREATING MEDICAL CONDITIONS BY POPULATION BASED ENCODING OF NEURAL INFORMATION

(71) Applicant: CASE WESTERN RESERVE UNIVERSITY, Cleveland, OH (US)

(72) Inventors: Dustin Tyler, Highland Heights, OH (US); Daniel Tan, Cleveland, OH (US); Matthew Schiefer, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/651,433

(22) PCT Filed: Dec. 16, 2013

(86) PCT No.: PCT/US2013/075329
§ 371 (c)(1),
(2) Date: Jun. 11, 2015

(87) PCT Pub. No.: WO2014/093964
PCT Pub. Date: Jun. 19, 2014

(65) Prior Publication Data
US 2015/0328465 A1    Nov. 19, 2015

Related U.S. Application Data

(60) Provisional application No. 61/737,484, filed on Dec. 14, 2012, provisional application No. 61/774,978, filed on Mar. 8, 2013.

(51) Int. Cl.
*A61N 1/36*    (2006.01)
*A61N 1/05*    (2006.01)

(52) U.S. Cl.
CPC .......... *A61N 1/36003* (2013.01); *A61N 1/0551* (2013.01); *A61N 1/361* (2013.01); *A61N 1/36014* (2013.01); *A61N 1/36103* (2013.01); *A61N 1/36146* (2013.01)

(58) Field of Classification Search
CPC ............ A61N 1/0551; A61N 1/36003; A61N 1/36014; A61N 1/361; A61N 1/36103; A61N 1/36146
See application file for complete search history.

(56) References Cited

U.S. PATENT DOCUMENTS 7,647,115 B2 *   1/2010  Levin et al. ..................... 607/44
2010/0286748 A1   11/2010 Midani et al.

FOREIGN PATENT DOCUMENTS

WO        0247757 A2    6/2002
WO     2012129574 A2    9/2012

OTHER PUBLICATIONS

International Search Report for PCT/US2013/075329, mailed Mar. 3, 2014, pp. 1-2.

*Primary Examiner* — George Manuel
(74) *Attorney, Agent, or Firm* — Tarolli, Sundheim, Covell & Tummino LLP

(57) ABSTRACT

The present invention generally relates to patterned intensity modulation of neural tissue. Certain embodiments provide a method of treating medical conditions by providing an electrode and modulating stimulation parameters delivered by the electrode. The stimulation parameters that are modulated relate to stimulation intensity and are varied according to a stimulation input parameter or time. The stimulation input parameter can be a choice of an individual waveform (i.e. Ψ or psi), which may be varied for each pulse.

20 Claims, 5 Drawing Sheets

METHODS OF TREATING MEDICAL CONDITIONS BY POPULATION BASED ENCODING OF NEURAL INFORMATION

TECHNICAL FIELD

The present invention relates to methods of treating medical conditions by employing patterned intensity modulation of neural tissue.

BACKGROUND

Sensory perception is a complex process that involves many circuits and levels of processing in the neural pathways before it reaches conscious perception. Loss of sensation is one of the more devastating consequences of upper limb amputation. Natural sensation is critical in an artificial limb. Sensation is important for fine motor control, an individual's sense of self, perception, and affective communication. No viable chronic replacement for sensation has previously been demonstrated. Those with limb loss must rely on visual and auditory feedback from the device motors for prosthesis control. The prosthesis is perceived by the user as a foreign tool extending beyond, but not as part of, the user's body. In addition to improved control of the prosthetic limb, sensory perception is important to providing a sense of embodiment and in the reduction of phantom pain.

SUMMARY

As stated above, sensory perception is a complex process that involves many circuits and levels of processing in the neural pathways before it reaches conscious perception. By stimulation of sensory pathways in subjects that can directly describe the sensations of the stimulation, it is possible to gain insight into the processing of these circuits. While the description is based on the sensory system, embodiments of the present invention extend to any neural input to a higher level processing neural system.

The present invention generally relates to patterned intensity modulation of neural tissue. Certain embodiments provide a method of treating medical conditions by providing an electrode and modulating stimulation parameters delivered by the electrode. The stimulation parameters that are modulated relate to stimulation intensity and are varied according to input parameters and time. Intensity refers to the parameters of any particular pulse waveform that affects the number of neural fibers activated by the stimulation pulse. In general, the parameters that affect intensity vary in a pattern or function that is not a scalar or is not the same distorted waveform shape produced by the input parameters. The intensity of stimulation can be varied as either a function or pre-defined pattern that is dependent on inputs, variables, and/or time. In addition to intensity of stimulation, even the choice of each individual pulse waveform (i.e. $\Psi$ or psi) may be varied for each pulse. Such a mode of patterned-intensity stimulation is referred to herein as a "population-based encoding" of neural information where the intensity and pulse shape determines which of the patient's axons are activated. By varying the population recruitment in a patterned fashion, information is introduced into the neural system by way of altering the "population" code. Non-limiting examples of neural tissue that can be modulated are axons or fibers of a nerve such as a peripheral nerve including an autonomic nerve or a somatic nerve. Autonomic nerves include parasympathetic and sympathetic nerves. The neural tissue can also be axons of the central nervous system, such as axons of the brain or spinal cord or their divisions.

In an embodiment, the present invention provides a method of introducing more information to a neural system of a patient through a population code. The method comprises placing a therapy delivery device in communication with a patient's neural tissue and activating the therapy delivery device. The method further comprises varying a stimulation parameter and field within the patient's neural tissue to change the population of fibers of the neural tissue that are active.

In another embodiment, the present invention provides a method of treating a medical condition in a patient suffering therefrom comprising placing a therapy delivery device in communication with the patient's neural tissue and activating the therapy delivery device. The method further comprises modulating a stimulation parameter delivered by the therapy delivery device. The stimulation parameter relates to stimulation intensity and varies according to a stimulation input parameter and time.

In another embodiment, the present invention provides a method of improving sensory perception in an individual in need thereof. The method comprises placing an electrode in communication with the patient's neural tissue and activating the electrode. The method further comprises modulating a stimulation parameter delivered by the electrode. The stimulation parameter relates to stimulation intensity and varies according to a stimulation input parameter and time.

BRIEF DESCRIPTION OF THE DRAWINGS

FIG. 1 illustrates the stability and selectivity of implanted cuff electrode systems according to embodiments of the present invention.

FIG. 2 illustrate waveform patterns. FIG. 2D (bottom plot) illustrates the resulting stimulation waveform where the interpulse interval (IPI) is 0.1 sec (10 Hz). Stimulation trials typically used an IPI of 0.01 sec (100 Hz) according to exemplary methods of the present invention.

FIG. 3 is a full-scale modulation, sinusoidal PW envelope.

FIG. 4 illustrates small-scale, offset (SSO) modulation.

FIG. 5 illustrates functional tasks with sensory feedback.

DETAILED DESCRIPTION

The disclosure herein may refer to "treating" certain medical conditions. This does not necessarily mean curing the medical condition but includes improving or minimizing the patient's symptoms. A medical condition' includes any biological function, disease, or disorder where improvement in the patient's condition is desired. A "patient" is a mammal and preferably is a human being suffering from an undesirable medical condition. A "therapy delivery device" includes any device that can stimulate a patient's neural tissue, including, but not limited to, an electrode/lead and/or a catheter/drug pump. Further, as used herein with respect to a described element, the terms "a," "an," and "the" include at least one or more of the described element unless otherwise indicated. Further, the term "or" refers to "and/or" unless otherwise indicated.

In addition, it will be understood that when an element is referred to as being "on," "attached" to, "connected" to, "coupled" with, "contacting," in "communication with," etc., another element, it can be directly on, attached to, connected to, coupled with, contacting or in communication with the other element or intervening elements may also be present. In contrast, when an element is referred to as being, for example, "directly on," "directly attached" to, "directly connected" to, "directly coupled" with, "directly contacting," "directly in communication with" another element, there are no intervening elements present.

Embodiments of the present invention provide neural interfaces to chronically elicit stable, repeatable, and natural tactile percepts in humans with upper limb amputation. Such neural interfaces can produce multiple, independent sensory perceptions over the entire phantom hand. Stimulation parameters are also provided. For example, changing the parameters of a time-varying pattern of stimulation intensity produce multiple, complex, natural sensations in a single location. Such parameter changes can produce a variety of exemplary touch perceptions such as tapping, constant pressure, light moving touch, and vibration in a subject's with limb amputation. Percept area and intensity can be controlled by stimulation strength and frequency, respectively. According to embodiments of the present invention, sensation at the fingertips and sensation of the opening span of the artificial hand enables the subject to perform delicate manipulations not otherwise possible. With sensation, a subject can better integrate an artificial hand as a natural part of themselves.

Embodiments of the present invention provide a neural interface for the chronic restoration of tactile perception. Such a neural interface can be used for artificial limbs. An embodiment of a device of the present invention comprises nerve cuffs containing multiple, independent stimulus channels. Each cuff can be implanted around a peripheral nerve, avoiding piercing protective neural tissues.

Figures 1A, 1B, 1C, 1D, 1E:
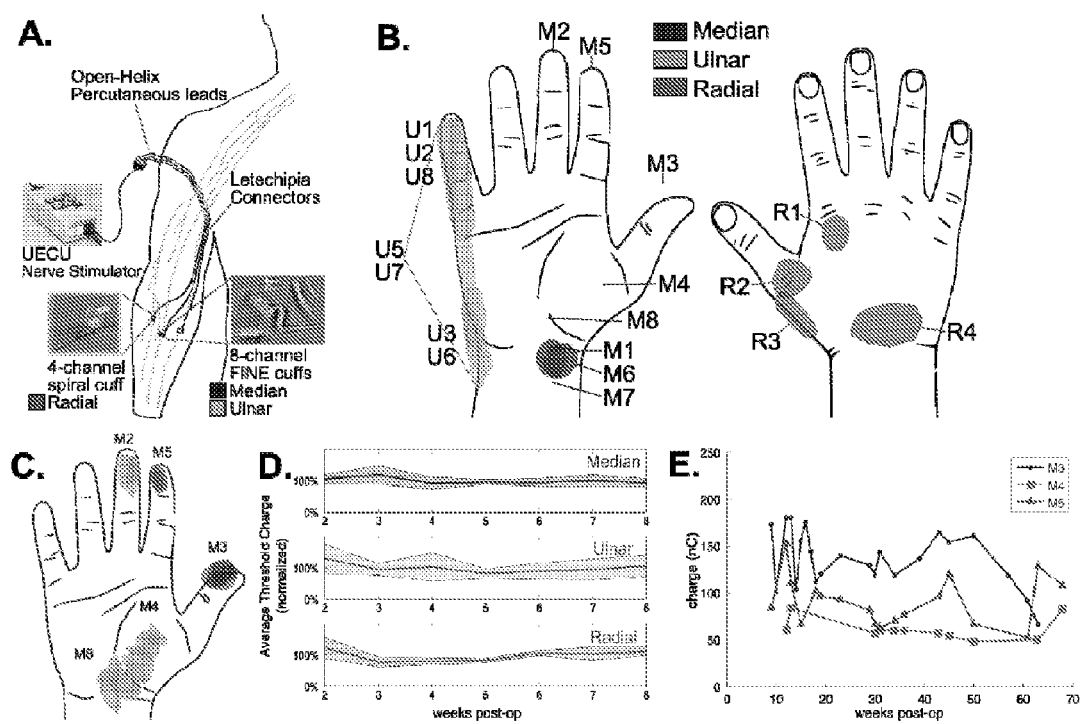
FIG. 1A schematically illustrates three cuffs with 20 channels that were implanted in the forearm of a subject: a 4-contact spiral cuff on the radial nerve of the forearm and 8-contact FINEs on median and ulnar nerves. Electrode leads were tunneled subcutaneously to the upper arm and connected to open-helix percutaneous leads via Letechepia connectors. Single-channel, charge-balanced, mono-polar stimulation was provided with the Universal External Control Unit (UECU) nerve stimulator.
FIG. 1B schematically illustrates typical sensation locations at threshold stimulation levels at week 3 post-operatively. Cuff electrodes were highly selective, with each contact (M1-8, U1-8, R1-4) producing either a unique location or unique sensation. Ulnar locations presented the most overlap at threshold, but differentiated in suprathreshold responses. Areas drawn outside of the hand borders indicate extension of percept area around the curvature of the digit. Since diagrams are based on subject drawings, some shift in location may be attributed to subject error.
FIG. 1C schematically illustrates repeated, weekly overlapping threshold locations of channels M2, M3, M4, M5, and M8 over weeks 3 through 10 Post-op indicated consistent location perception. These locations were prioritized due to their potential for hand grasp sensation feedback. Locations remained relatively stable regardless of stimulation waveform used.
FIG. 1D is a chart illustrating mean, normalized charge density for all channels on the median (blue), ulnar (green), and radial (red) cuffs shown as the solid line. Shaded areas indicate the 95% confidence interval, with no indication of raising thresholds. An unbiased, step-wise search determined the threshold. Frequency was held constant at 20 Hz.
FIG. 1E is chart illustrating that threshold tracking of median channels M3, M4, and M5 to 68 weeks and ongoing show no significant change in threshold over time (p=0.053, 0.587, 0.773 respectively).

As described in more detail below, three nerve cuff electrodes were placed around nerves in the forearm of one amputee with a wrist disarticulation and in the upper arm of a second amputee with a below elbow amputation as schematically depicted in FIG. 1A. One subject had been implanted for over 18 months and the second for over 11 months. The selected interface technologies were a self-sizing spiral nerve cuff electrode and 8-channel Flat Interface Nerve Electrodes (FINE). The FINE maintains the nerve in an oblong configuration to facilitate selective stimulation. The stable and selective nature of the cuffs for more than a year enabled stimulation waveforms that restored natural, tactile sensation without the "tingling," or paresthesia, typically associated with electrical stimulation. Sensory feedback improves patients' performance on functional tasks and increased their sense of embodiment of the prosthesis. Other attempts have used direct peripheral nerve stimulation to produce sensation. Single-channel nerve cuff electrodes produced sensation in the perceived hand nearly four decades ago, although first clenching, vibration and paresthesia were the primary responses to stimulation. More recently, intrafascicular electrodes implanted in the nerve could produce some tactile sensation but were only a short-term solution and exhibited a continuous threshold increase and full loss of functionality as early as 10 days. Paresthesia was associated with ~30%-50% of the stimulating channels in intrafascicular studies.

Alternative methods to direct nerve stimulation have been explored to restore sensation to amputees. Sensory substitution applies a surrogate sensation, typically vibration at a distant location on the body, to provide information about the lost sensation, such as pressure at the prosthetic finger tips. The substituted sensation requires interpretation both in terms of mode (vibration encodes pressure) and location (sensation on the chest encodes what is occurring at the fingertips). Sensory substitution currently serves as the primary alternative for providing sensory feedback and has been shown, in fact, to improve prosthetic control in limited situations. However, this technique has not been widely adopted, possibly because the vibration may become more disturbing than helpful if activated too long and interpretation of the substitution requires mental effort. It rarely becomes "natural" like the lost sensation.

Another alternative method is cortical stimulation, in which electrodes are inserted into the sensory cortex of the brain. For example, in certain embodiments, distributed, punctate sensations may be created and controlled across the phantom hand.

The described multi-channel nerve cuff electrodes produce chronic, stable, and selective restored sensation in humans. Such electrodes and accompanying devices provide stable, multiple, and natural tactile sensations at many punctate locations.

Peripheral Interface is Selective and Stable

In weekly experiments, monopolar electrical nerve stimulation on any one of 20 possible channels implanted around the median, radial, and ulnar nerves of the subject was provided as schematically illustrated in FIG. 1A. The threshold for sensory perception was determined by slowly increasing the stimulus intensity until the subject indicated that he felt something. For each supra-threshold stimulus, the subject verbally described the sensation and sketched the perceived location on a hand drawing. Of the 20 available channels, stimulation produced sensation at 19 unique locations on the perceived limb as schematically illustrated in FIG. 1B, illustrating the high degree of selectivity achieved with the multi-channel cuffs. The locations of percepts were repeatable and stable as indicated by FIG. 1C. Percepts were produced at many locations, but included thumb and index finger tips, which were highly desirable because the prosthetic hand typically applies force at those locations during functional tasks. All perceived locations were consistent with innervation patterns for the respective median, ulnar and radial nerves on which the electrodes were implanted, suggesting that the sensory pathways from the amputated limb and the subject's perception are not affected by cortical remapping, confirming earlier short-term studies.

In addition to stable locations, the minimum amount of stimulation required to produce sensation, i.e. threshold, remained stable. During weeks 2-8, percept thresholds were 95.5±42.5 (n=59), 70.7±59.2 (n=50), and 40.7±12.4 nC (n=24) for the median, ulnar and radial nerves, respectively. Linear regression over 8 weeks for every channel showed thresholds did not change (18/19) or decreased (1/19), strongly suggesting stimulation, nerve, and electrode stability ($p<0.05$, FIG. 1D). Further threshold tracking up to 68 weeks and ongoing, on select channels, show a continuing trend of stability (FIG. 1E).

Muscle contractions were not observed during stimulation, which was as expected, since the cuffs were implanted distal to the motor branches of all residual muscles. Further, stimulation artifact did not interfere with myoelectric control. The subject participating in this study is a very vigorous myoelectric prosthesis user and has, on multiple occasions, broken his prosthetic hand. Thus, despite the stresses the subject continues to apply to his body and prosthesis, embodiments of the present invention provide a selective and reliable neural interface for sensory feedback in active individuals.

Stimulating with Time Invariant Parameters Produces Paresthesia

Figures 2A, 2B, 2C, 2D:
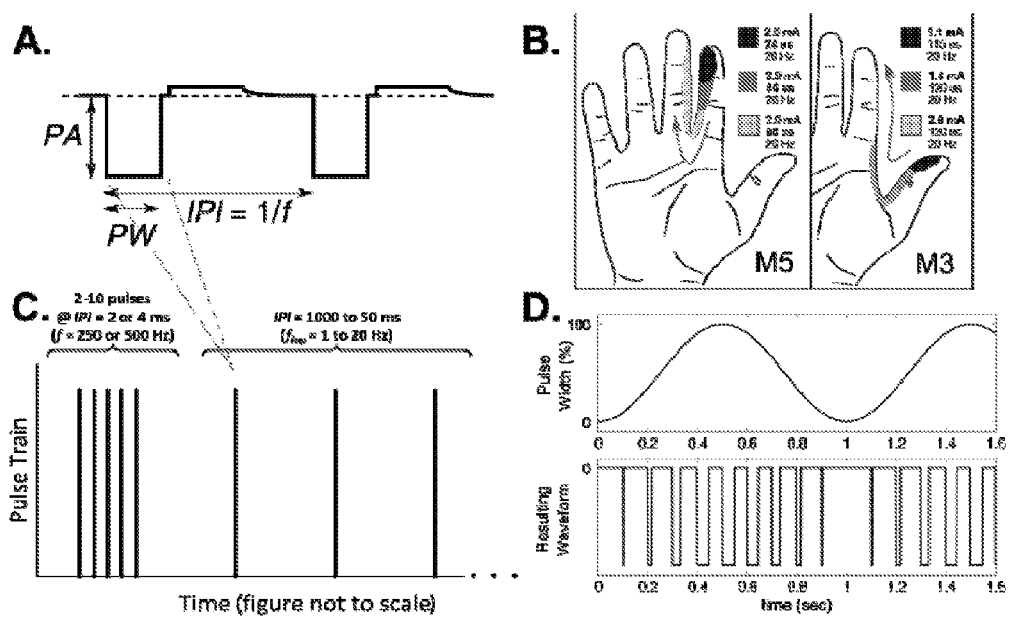
FIG. 2A is a classic square, charge-balanced, cathodic-first stimulation pattern. Parameters such as pulse amplitude (PA), pulse width (PW) and interpulse interval (IPI) or frequency (f) are held constant in most neural stimulation paradigms.
FIG. 2B is schematic illustration of a percept area of a subject. In general, PA and PW modulated the percept area of recruitment at suprathreshold levels with constant parameter stimulation. M5 showed a channel-specific recruitment pattern as PW was increased from 24 to 60 μs. M3 showed that percept area recruitment also was achieved by increasing PA from 1.1 to 2.0 mA. These recruitment patterns match digital nerve innervation patterns.
FIG. 2C is a variable frequency, bursting pattern where constant frequency, $f_{tap}$, stimulation was pre-pulsed with 2-10 pulses at 250-500 Hz resulted in a tapping sensation. Constant stimulation alone produced paresthesia.
FIG. 2D (top plot) is an example of a full-scale modulation, using a sinusoidal (1 Hz) PW envelope that produces a natural sensation of pulsing pressure.

Nerve stimulation classically comprises a train of identical charge-balanced, electrical pulses characterized by pulse amplitude (PA), pulse width (PW), and pulse repetition frequency (f) or interpulse interval (IPI=1/f) as depicted in FIG. 2A. Traditionally, these three parameters are time invariant and fixed in value: $PA(\phi_t)=PA_0$, $PW(\phi_t)=PW_0$, and $IPI(\phi_t)=IPI_0=1/f_0$. Several variations of $PW_0$, $PA_0$, and $f_0$, were explored and the resulting sensations were mapped. When constant pulse trains were applied, the subject consistently reported an unnatural sensation of paresthesia, described as "electrical," in 96% of 151 trials over a 10-month period. For all frequencies between 1 and 1,000 Hz that were tested, paresthesia remained the dominant sensation. There was a weak relationship between frequency and the perceived intensity and size of the percept area. Increasing $PA_0$ or $PW_0$ increased the intensity and/or percept area in a monotonic fashion as shown in FIG. 2B. Although not wishing to be bound by theory, this is likely the result of recruiting additional sensory fibers from the same dermatome that were co-localized within the peripheral nerve Infrequently, paresthesia was accompanied by a sense of pressure, but it was masked by the tingling of paresthesia. During stimulation applied up to 60 sec, paresthesia never resolved into a natural sensation, as has been previously reported.

While the selectivity and stability of the perceptions induced by constant parameter stimulation was encouraging, the inability to produce natural sensations spanning the range of somatosensory modalities remained a major limitation.

Consequently, we different stimulus trains were applied in which parameters varied as a function of time.

Stimulating with a Time-Variant Pulse Width, $PW(\phi_i,t)$, Results in Natural Pressure Perception Full-Scale Modulation Feels Like a Pulse.

Figures 3A, 3B, 3C:
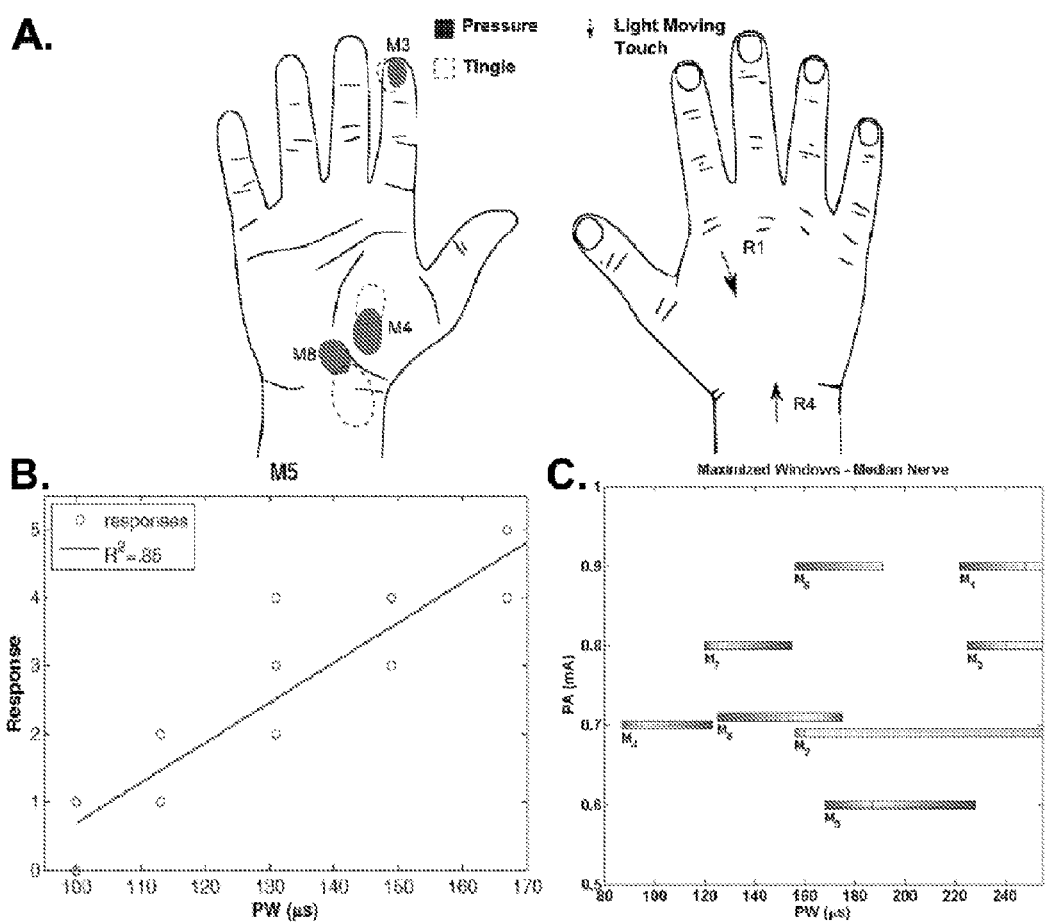
FIG. 3A schematically illustrates that at threshold ($B_{th}$), a pulsing pressure was felt at the bold circle area (M3, M4, M8, blue). Increasing the PW to a secondary threshold ($B_{tingle}$) introduced an additional pulsing paresthesia, which typically covered a larger area that overlapped the pressure location. Increasing the PW further caused the area of paresthesia to increase while the area of pressure did not. Light moving touch was described as if someone were lightly brushing their skin with a finger, and was consistently unidirectional for a given stimulus parameter set (R1, R4, red).
FIG. 3B is a chart of a psychometric rating of $PW_{max}$ Indicating a Clear Relationship Between PW and the Strength of the perceived intensity. The subject was provided 5 $PW_{max}$ levels (100, 114, 131, 150, 167 μs) and each level was presented 3-6 times in random order.
FIG. 3C is a chart illustrating threshold windows for natural sensation measured on every channel of a median cuff. Pressure occurred at $B_{th}$ (green), was accompanied by paresthesia at $B_{tingle}$ (black line, yellow), and was overwhelmed by paresthesia at $B_{Mask}$ (red). The largest PW windows for a particular channel were found when PA was lowest. Higher levels of stimulation were avoided for M6 due to pain response.

Variation in stimulation, therefore, is important to perception, but tapping is not as useful as perception of pressure. The pulse width was modulated with a slow ($f_{mod}$=1 Hz) sinusoidal envelope, rather than holding pulse width constant throughout the train. The pulse width, therefore, ranged from 0 μs to B μs (see FIG. 2D and methods below). In response to such stimulation, the subject reported a natural pulsing pressure sensation at 1 Hz and described it, "as if I was feeling my own pulse or heartbeat, just like putting my fingers here," as he demonstrated his fingers against his jugular pulse in the neck. When the peak pulse width was set to the first noticeable level, $B_{th}$, the sensation was described as repeatedly pushing "very lightly" on a spatially localized area of the skin as indicated by FIG. 3A. When the subject was asked to tap in synchrony using the intact limb for visual confirmation, the tap matched the frequency, $f_{mod}$. As B increased, the sensation became pulsing pressure with increasing intensity, but with the same frequency of $f_{mod}$. To determine if perceived intensity varied with pulse width, the subject was asked to rate his perception of 5 different values of peak pulse width, B. The subject's verbal rating of perceived intensity correlated significantly with B ($p<0.05$, $R^2$=0.85, n=22) as indicated in FIG. 3B. The sensation was always described as "natural" for all locations of sensation on the hand when the pulse width was varied according to this pattern. At the finger tips, the pulsing sensation was described as similar to pressing on the tip of a ball-point pen. The perceived sensory modalities across all 19 active channels and all trials included pulsing pressure (86.1%), light moving touch (7.3%), or tapping (7.3%). The response to the modulated pulse width stimulation on all channels during a single experimental sessions and aggregated over multiple sessions is shown in Table 1 and Table 2. Table 1 shows example sensation modalities during a single experimental session. Channels were modality specific. Pressure was as if a finger was pressing on the area unless otherwise described. M6 transitioned to a sensation of a needle within a vein at higher stimulation. U4 occasionally produced sensation and was thought to be located on the edge or off the nerve. Table 2 shows average channel response for each cuff with full-scale modulation, where n is the number of unique, natural responses per channel, per experimental visit. Natural, non-tingling sensation was achieved on every channel with sinusoidal varying PW stimulation. Columns may not sum to 100% since some observations lead to multiple sensations.

TABLE 2

Summary of full-scale modulation, sinusoidal (1 Hz) PW Results (average channel response)

| | Median (n = 45) | Ulnar (n = 24) | Radial (n = 13) |
|---|---|---|---|
| Pressure (Pulsing or Tapping @ 1 Hz) | 85.0% | 86.5% | 87.5% |
| Moving Touch | 8.8% | 3.1% | 12.5% |
| Vibration or Tapping (>1 Hz) | | 7.3% | |
| Discomfort or Pain | 6.8% | 3.1% | |

The range of B was then identified that results in a natural sensory percept such that $B_{th}<B<B_{tingle}$. When $B>B_{tingle}$, the subject reported a light tingle sensation in addition to the natural percept as indicated by FIG. 3A. When B is further increased past a certain limit ($B_{Mask}$), such that $B>B_{mask}>B_{tingle}$, paresthesia dominated the natural sensory perception as indicated by FIG. 3C.

Small-Scale, Offset (SSO) Modulation Feels Like Constant Pressure.

The stimulation waveform was refined further to produce the perception of constant pressure rather than a pulsing pressure. We found that by raising the lower pulse width from 0 μsec up to threshold levels, the subject felt smaller pulsing and a more lingering pressure during the sinusoidal pulse width modulation. When the modulation was very small, the subject felt continuous pressure that he described as, "as natural as can be," and "like someone just laid a finger on my hand." The typical size of pulse with modulation, $PW_{pk-pk}$, was surprisingly as small as 5 μs. The stimulation pulses had an $IPI_0$ of 0.01 sec and the modulation envelop frequency, $f_{mod}$, was 1 Hz. The $PW_{offset}$ was set to approximately 90% of the $B_{th}$ required to produce the natural pulsing sensation (see FIG. 4A and methods below). Constant pressure on all locations on the palmar side (M2, M3, M4, M5, U1) for all channels was achieved as shown in Table 3. A $PW_{pk-pk}$ of 1-10 us when $PW_{offset}$ was set to the appropriate level generated a sensation of continuous pressure. If the $PW_{pk-pk}$ or $PW_{offset}$ was too large or too small, the resulting sensation was either paresthesia or the natural sensation generated by full-scale modulation.

TABLE 1

| Median Contact | Modality | Ulnar Contact | Modality | Radial Contact | Modality |
|---|---|---|---|---|---|
| M1 | Light moving touch | U1 | Pressure | R1 | Pressure/light moving touch |
| M2 | Pressure | U2 | Pressure on bone | R2 | Pressure |
| M3 | Pressure of ball-point pen | U3 | Pressure on bone | R3 | Pressure/Tingling |
| M4 | Pressure | U4 | Pressure of ball-point pen | R4 | Pressure/Light moving touch/Foam texture |
| M5 | Pressure of ball-point pen | U5 | Tingling Pulse | | |
| M6 | Uncomfortable, deep, dull vibration. | U6 | Light moving touch, tickle | | |
| M7 | Light moving touch | U7 | Pressure | | |
| M8 | Pressure | U8 | Pressure on bone | | |

TABLE 3

| Constant Freqs: 5-500 Hz Constant PAs: 0.6-0.8 mA | Median ($PW_{pk-pk}$) | | | |
|---|---|---|---|---|
| Sinusoidal PW ($F_{envelope}$ # 1 Hz) | M2 | M3 | M4 | M5 |
| Constant Pressure | 5 uS, (n = 8) | 2-5 uS, (n = 22) | 1-10 uS, (n = 79) | 2-5 uS, (n = 12) |

Figures 4A, 4B, 4C:
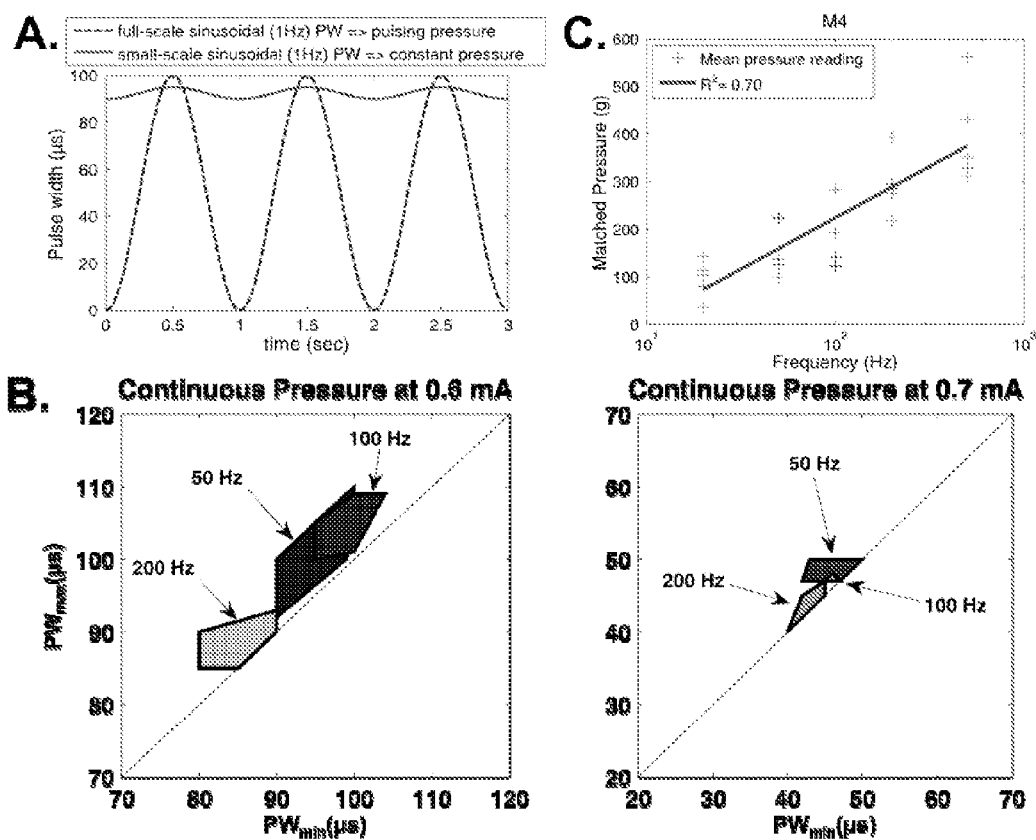
FIG. 4A is a typical example of a SSO modulation using sinusoidal (1 Hz) PW with offset stimulation on M4 (solid, red line). $PW_{pk-pk}$=90-95 μs was the lowest stimulation level that produced constant pressure sensation. For comparison, the threshold for pulsing pressure from full-scale modulation is shown (dotted, blue line).
FIG. 4B is chart illustrating that the $PW_{min-max}$ window that produced a sensation of constant pressure was strongly influenced by the PA, which altered both the size and the location of the window. Frequency was found to have a weaker effect on the window but was found to affect the intensity (D). At PA of 0.5 mA there was no response. For PA 0.8 mA and above, the data suggests that the window for continuous pressure sensation decreases.
FIG. 4C is a chart illustrating that contralateral pressure matching indicated frequency can control intensity of constant pressure sensation. The subject was provided SSO modulation with IPI set to 50, 20, 10, 5 or 2 ms (20, 50, 100, 200 or 500 Hz) on channel M4 and asked to match the perceived pressure with his contralateral hand. Perceived constant pressure intensity was on the order of 0-500 grams (<1 lb).

The size and range of the $PW_{pk-pk}$ window needed to produce constant pressure was found to be dependent on the stimulation channel, $PA_0$, $PW_{offset}$, and IPI as indicated in FIG. 4B. To confirm that the natural sensation was a consequence of the modulation of the stimulation, as $PW_{pk-pk}$ decreased toward zero, the percept transformed back to paresthesia. Subsequently increasing $PW_{pk-pk}$ returned the sensation to that of continuous pressure. As $PW_{offset}$ increased, the subject reported an increase in intensity. When the maximum pulse width exceeded $B_{tingle}$, pressure was accompanied by paresthesia. Therefore, there is a window for generation of natural sensation dependent on time-varying characteristic of the stimulation and the strength of the stimulation.

Stimulation Frequency Controls Intensity of Natural Sensation.

Axonal firing frequency is commonly understood to encode intensity of pressure in microneurography studies. Without wishing to be bound by theory, since a sensation of constant pressure was possible at a fixed frequency, it is believed that perception of intensity of the constant pressure could be modulated with the pulse repetition frequency (f=1/IPI). The subject was presented with an initial stimulation pulse rate with the IPI=0.02 sec and instructed that the perceived intensity was defined as "5." He then scored subsequent sensations relative to the initial sensation. The lightest intensity (score 1) occurred at the longest IPI (0.2 sec) and the subject described the sensation as if, "a finger was just resting on the surface of the skin." The greatest intensity (score 13) was at the shortest IPI (0.002 sec) and was reported as "white knuckle" forceful pressure. In another experiment, the subject was asked to press on a pressure sensor with the contralateral limb that was matched to the perceived shape and location of the sensation on the phantom limb. There was a direct relationship between the IPI and matched pressure sensation (p<0.05, R=0.70, n=25) as indicated in FIG. 4C.

Sensory Feedback Improves Functional Performance

Figures 5A, 5B, 5C, 5D:
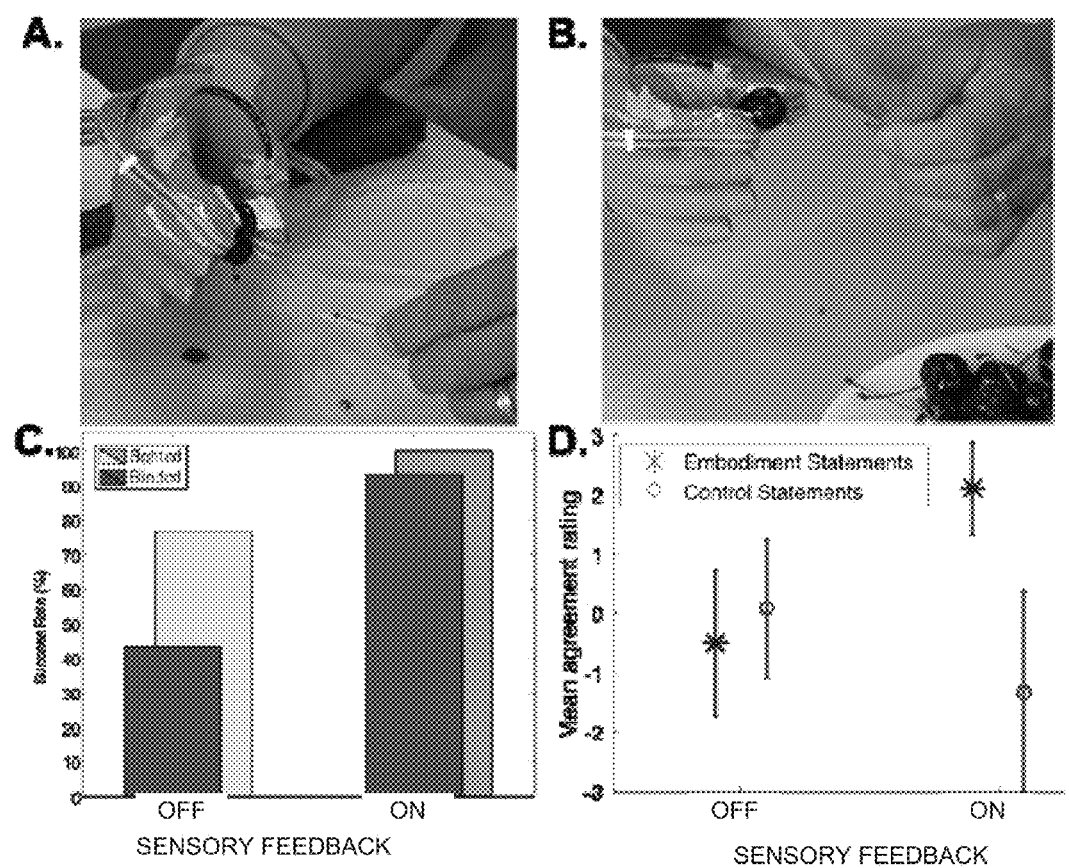
FIG. 5A is a photograph depicting that without the sensory feedback system enabled, the subject was unable to provide an appropriate amount of grip force in a delicate task of holding a cherry while removing the stem.
FIG. 5B is a photograph illustrating that with the sensory feedback enabled, the subject knows when contact occurs and can successfully grip the cherry without damaging the fruit.
FIG. 5C is a chart illustrating that sighted and blinded performance with the sensory feedback on or off during the cherry task shows a clear improvement in functional capability, even under sighted conditions.
FIG. 5D is a chart illustrating that ratings for embodiment statements on the Embodiment Questionnaire show a significant agreement over control statements when sensory feedback is on and an significant improvement from functional task experiences without sensory feedback.

The ultimate goals of restoring sensation are to improve functional use of the prosthesis, improve subject confidence using the prosthesis, and provide a sense of embodiment with the prosthesis. Sensation is critical to performance of tasks that require more precise control of the grasp pressure. To test the enhancement of control with sensation, the subject plucked the stem off of a cherry with his intact hand while holding the cherry with his prosthetic hand. Thus, the subject had to apply enough pressure to the cherry to secure it in order to remove the stem without applying too much pressure that damaged or crushed the cherry as indicated by FIGS. 5A and 5B. The test was administered with and without providing sensory feedback to the subject through force-sensitive-resistor sensors mounted on the fingertips of the prosthetic hand. In both cases, half of the tests were administered while the subject could see the cherry being grasped and hear the prosthesis motors and the other half had vision and hearing 100% occluded.

When sensory feedback was not provided, the subject successfully plucked 43% and 77% of the cherries when blinded or sighted, respectively. When sensory feedback was provided, the subject successfully plucked 93% and 100% of the cherries when blinded or sighted, respectively, as indicated by FIG. 4C. Using a test of two proportions, sensory feedback was found to significantly improve performance while blinded (p<0.001). Sensation is critical to controlled grasp without sight. Performance with sensation was significantly improved (p<0.005) and actually maximized (100% correct) in the sighted case. Thus, sensation improves performance, even when the user can see their prosthesis. Without sensation, the prosthesis is often used only for gross tasks such as bracing and holding.

In addition, the subject expressed greater confidence in his functional capability and higher embodiment when the sensory feedback was enabled. A one-tailed t-test of the subject's self-reported confidence during each functional trial showed a significant increase in confidence (p=0.0305). An adapted prosthesis embodiment survey (3, 17) was provided after conducting functional tasks with and without sensory feedback. A significant improvement was found for the ratings of statements correlating with prosthesis embodiment with sensory feedback (p=0.002) suggesting an increase in subjects sense of embodiment as indicated in FIG. 4D. These results support the idea that sensation will enable finer activity, improve bilateral activities, and hence, a more normal appearance and integration of the prosthesis into self-image and improved confidence.

Discussion

Methods of the present invention relate to chronic, multi-location, multi-perception sensory feedback system to improve functional performance and quality of life. By changing the paradigm of electrical stimulation, sensory perception is controlled. By independently controlling pulse width, pulse amplitude, stimulation frequency, and the patterns by which these parameters are varied, potential control of the spatial extent, intensity, and quality of perception has been demonstrated. The electrodes are able to attain this level of control in multiple spots of a single nerve such that there is a complete and independent control of 19 different locations on the hand with only three implanted cuffs with a total of 20 electrical contacts. These results remain stable, reliable, and repeatable for over 18 months without any evidence suggesting it will change going forward. The system is robust to heavy normal daily activity of the subject.

Tasks requiring fine prosthesis control, e.g. pulling the stem from a cherry, which were not reliably possible without sensation even when sighted, are made possible with sensory feedback, even when blinded. Sensation will alleviate the visual and attentional demand typically required to use a myoelectric prosthesis. Feeling the grasp of an object and the pressure applied further augments confidence in task performance. Moreover, the subject reports feeling like he is grabbing the object, not just that he is using a tool to grab the object.

Compared to the elegant and often complex experiments in non-human primates to indirectly assess the effects of sensory stimulation, the subject could directly express the perception elicited by stimulation. This immediate and detailed feedback allowed for new stimulation embodiments of time-varying patterned stimulation for control of perceptual quality.

Without wishing to be bound by theory regarding the mechanism of controlling sensory perception, it is believed that the time-variant stimulus train recruits spatially distinct populations at different times, creating a non-uniform pattern of activation. For example, with respect to the SSO modulation paradigm, at the lowest pulse width, a small population of axons is supra-threshold and actively firing. Because the pulse width never decreases below this level, this population of the neurons will always activate at the stimulation frequency, which is a constant, SA-type pattern. Only at higher pulse widths will there be sufficient stimulation to activate other, more distant neurons. That population will have a more transient or pulsing activation pattern that mimics the pattern more typical of RA/PC fibers. It is unlikely either population consists of entirely SA type fibers or RA/PC type fibers. Thus, the resulting activation pattern is not strictly natural. However, the results described herein would suggest that the upstream processing in the thalamic relays and columns of the primary sensory cortex are sufficiently robust to correct for errors in the pattern to produce natural sensory perception. Normal processing in the brain is highly tolerant of abnormal patterns and classifies patterns according to best matching prior sensory experience. Optical illusions are examples of this property of the brain's classification ability. Therefore, we theorize that as long as a sufficient population of SA fibers is continuously activated and a sufficient population of RA/PC fibers are transiently activated, the brain can interpret the stimulation as being produced naturally by pressure applied to the phantom hand.

The subject's comments as described herein were particularly poignant. The subject strongly preferred having sensory feedback, which he described as natural, requiring no additional interpretation, unlike sensory substitution methods. When asked about performing tasks with sensory feedback enabled, he always stated that, "I knew that I had it," referring to whatever object was part of the test. He repeatedly expressed a desire for a fully-implanted take-home system that provided him with permanent sensation ("I'd rather have it. I'd rather have it in a heartbeat."). When sensation was active, the subject's perceived hand and prosthetic hand nearly perfectly aligned. However, when sensation was not active, the prosthesis was viewed by the subject as an extension beyond his hand. The subject reported episodic phantom pain several times a month. He has remarked that since the implantation of the system 18 months prior, he has not had any episodes.

Regarding extraneural electrode selectivity, almost every contact provided sensation at well-defined and unique locations. The subject could identify sensation at multiple sites independently, even if the two sites were stimulated within the same cuff. There is evidence that peripheral nerves are somatotopically organized, and hence, multi-channel cuff electrodes are able to chronically produce somatotopically selective results, similar to those reported in acute trials with intrafascicular electrodes. Reports from acute trials with intrafascicular electrodes in two nerves at similar locations demonstrated sensation with 9 of 32 channels (28%). Conversely, embodiments of methods produced punctate sensations with 19 of 20 channels (95%). Intrafascicular electrodes implementing traditional, constant pattern stimulation paradigms were found to produce both paresthesia and some tactile percepts. Similar to the results described herein, intensity was modulated by the stimulation frequency. By introducing the time-variant stimulation embodiment, the quality of the sensation was controlled. By varying the stimulus patterns, constant pressure, pulsing pressure, flutter, tapping, vibration, or paresthesia with a single stimulation channel were produced and the perceptions were all at the same perceived location on the hand. More than 1.5 years after implant, these results continue to remain stable and do not show any indication that they will change.

CONCLUSION

Embodiments described herein provide chronically stable sensory neuromodulation system in a human that produces multiple modes of sensation at multiple points in the perceived hand and that perception significantly improves performance using a prosthesis. Time-variant modulation of stimulation controls perceived sensory quality and frequency of stimulation produces a natural, graded intensity of sensation. This is a fundamental shift in stimulation paradigms and can have applications in the neural interfacing and sensory modulation fields, particularly in applications with perception-related outcomes, such as pain.

Furthermore, although embodiments are described herein with respect to sensory perception, this population-based encoding by way of patterned stimulation intensity can apply to any suitable afferent or autonomic neural system that is an input to other neural systems such as, for example, somatosensory perception, autonomic control of homeostasis, and perception of pain. Other medical conditions or functions include modulation of pain by TENS, spinal cord stimulation, or any other suitable means of neural excitation for modulation of pain; taste; regulation of swallowing via stimulation of sensory afferents in the oral-pharyngeal tract; gastric reflux; autonomic regulation, such as blood pressure via baroreceptor stimulation, insulin regulation via stimulation of pancreatic nerves, and appetite via stimulation in the enteric nervous system; auditory restoration via cochlear nerve stimulation or cochlear implants; sexual sensation and/or enhancement; and/or incontinence, voiding and other genito-urinary regulation. Embodiments of methods can be used for, but not limited to, spinal cord stimulation, peripheral nerve stimulation, mechanical stimulation, and/or deep brain stimulation.

Embodiments of the present invention also apply to fields outside of the medical field. For example, methods of the present invention could provide sensory input in a haptic interface and could be used in robotics, gaming technology, and other man-machine interfaces.

EXAMPLES

Materials and Methods

Study Design

Without wishing to be bound by theory, it is believed that direct nerve stimulation with selective, non-penetrating peripheral nerve cuff electrodes on the residual upper limb nerves can elicit graded sensation and proprioception at multiple locations in the perceptual hand. After initial data suggested a stable nerve stimulation platform with multiple perceptual locations, the specific aim was to determine stimulation waveforms which would produce natural touch modalities without paresthesia.

The inclusion criteria for human subjects included upper-limb, uni-lateral amputees, age 21 and older, and who are current users of myoelectric prosthesis or prescribed to use one. Potential subjects were excluded for poor health (uncontrolled diabetes, chronic skin ulceration, history of uncontrolled infection, active infection) and if significant, persistent pain existed in the residual or phantom limb.

Methods

Surgeons implanted three electrodes in an outpatient surgical procedure. Multi-contact nerve cuff electrodes were placed in the residual limb of a 46 year-old male who has a unilateral wrist disarticulation from work-related trauma. At the time of implant, the subject was 18 months post-amputation and had been a regular user of a myoelectric prosthesis for 7 months. Eight-contact Flat Interface Nerve Electrodes (FINEs) were implanted on the median and ulnar nerves and a 4-contact spiral electrode was implanted on the radial nerve. FINE opening size for the nerve was 10 mm wide by 1.5 mm tall for both the median and radial nerves. The internal diameter of the spiral electrode was 4 mm for the radial nerve. Selection of electrode sizes was based on peripheral nerve histology studies in human cadavers and with confirmation by surgeons during the operation. All electrodes were in the mid-forearm as indicated by FIG. 1 and connected to percutaneous leads that exited through the upper arm. Implanted components (cuff electrodes, percutaneous leads, connectors) were manufactured by Ardiem Medical (Indiana, Pa.) and sterilized with Ethylene Oxide by Ethox International (Buffalo, N.Y.). The subject was discharged from the hospital the same day as the surgery.

The implanted electrodes were allowed to stabilize for three weeks before experimental stimulation was applied. During the recovery period, subject reported no adverse sensations in the implanted locations and no abnormal phantom sensations. In following weekly sessions, experimental stimulation was applied through each contact for up to 10 sec. For all trials, the subject was blinded to the stimulation. Following stimulation, the subject would describe any perceived sensation and sketch its location on a hand diagram. Trials with no stimulation were randomly intermixed to assure no subject bias.

Experimental Setup

The stimulation system includes a computer that controls stimulation parameters and sends the commands to a single board computer running xPC Target (Mathworks, Inc.). The stimulator is the Universal External Control Unit (UECU) and is controlled through the xPC Target. An isolator provides optical isolation between devices plugged into the wall and the subject. To prevent overstimulation, the charge density was limited to less than 50 $\mu C/cm^2$ and the stimulation kept to less than 50% duty cycle during all stimulation protocols.

The UECU is a custom stimulator manufactured by Ardiem Medical (Indiana, Pa.). It has 24 channels of controlled-current stimulation outputs, with a maximum stimulation amplitude of 5.6 mA, a maximum stimulation pulse width of 255 $\mu s$ and a compliance voltage of 50 V. The UECU provides monopolar, biphasic, charge-balanced, cathodic-first stimulation pulses with common anode. Anodic return was through a 2"×4" surface electrode on the dorsal of the upper arm immediately proximal to elbow.

Generic Framework of Electrical Stimulation

The generic stimulation waveform, $\Lambda$, is a train of pulses, $\Psi$, separated by an interpulse interval, IPI. For each pulse shape, the pulse parameters, $\Delta$, are selected to produce neural excitation. To elicit a sensory perception from touch, the pulse parameters, $\Delta$, and IPI are a function of measured external inputs over time, $\phi(t)$, and time, t. Sensory perception is a result of processing by higher-order neural circuits that are sensitive to both the activation and to the pattern of changes in activation of the peripheral receptor. To elicit natural sensory perception, stimulation of the peripheral nerve is expected to be dependent on changes in activation, so $\Delta$ and IPI are defined as a function of the desired tactile perception and time, i.e. $\Delta(\phi(t), t)$ and $IPI(\phi(t),t)$ (Eq. 1).

$$\Lambda(\phi,\Delta,t)=\Sigma_i \psi_i(\Delta_i(\phi_i),t-t_i) \forall t_i \leq t < t_{i+1}, \psi_i=\psi(t_i), \Delta_i=\Delta(t_i),$$
$$\phi_i=\phi(t_i) t_i=t_{i-1}+IPI(\phi_{i-1}) \quad \text{Eq. 1}$$

$\psi \triangleq$ Individual stimulus pulse waveform, such as square (FIG. 2.A)

$\Delta(\phi,t) \triangleq$ Stimulation waveform parameters $\phi(t) \triangleq$ The sensory data measurements This example reports on the psychometric relationships between modulation of stimulation parameters and sensory perception with $\psi$ as a charge-balanced, biphasic, square pulse, having parameters $\Delta=\{PA(\phi,t), PW(\Phi,t)\}$ with IPI(t), where PA is pulse amplitude and PW is pulse width. The findings show that perception is controlled by the time-dependent change of the parameters, referred to as time-variant modulation. Variation of each of the parameters of stimulation were systematically examined according to each of the following conditions.

Stimulating with Time Invariant Parameters $$PA(\phi_i)=PA_0, PW(\phi_i)=PW_0, \text{and } IPI(\phi_i)=IPI_0=1/f_0$$

Stimulating With a Time-Variant Frequency, $IPI(\phi_i,t)$

A bursting pattern is defined as $$IPI(\phi, t) = \begin{cases} 2 \text{ or } 4 \text{ ms} & \forall t \leq 50*N \text{ ms} \\ \dfrac{1}{f_{tap}} \text{ ms} & \forall t > 50*N \text{ ms} \end{cases}$$

where N is the number of bursting pulses, generally between 2 and 10 (FIG. 2.C).

Stimulating with a Time-Variant Pulse Width, $PW(\phi_i,t)$

Full-Scale Modulation.

For this set of trials, the stimulation parameters of Eq. 1 were slowly varied according to the following:

$$t_i=t_{i-1}+IPI_0$$

$$PA_i=PA_0$$

$$PW_i=a \sin(f_{mod}t)+b \quad \text{Eq. 2}$$

a and b are parameters that control the size of the pulse width modulation. In these trials, the interpulse interval was held constant at $IPI_0=0.01$ s. The pulse width was modulated in a slow ($f_{mod}=1$ Hz) sinusoidal envelope with b=a=B/2, where B is the peak of the varying pulse width. The pulse width, therefore, ranged from 0 $\mu s$ to B $\mu s$ as indicated in FIG. 2D.

Small-Scale, Offset (SSO) Modulation.

Small modulation was defined in Eq. 2 with $a=(PW_{max}-PW_{min})/2=PW_{pk-pk}/2$ and $b=PW_{offset}$. The typical value of $PW_{pk-pk}$ was 5 $\mu s$, $IPI_0$ was 0.01 sec, $f_{mod}=1$ Hz, and $PW_{offset}$ was set to approximately 90% of the $B_{th}$ required to produce the natural pulsing sensation as indicated by FIG. 4A.

Threshold Detection Method

Threshold was determined using the Single-Interval Adjustment Matrix, which is an unbiased, adaptive staircase method. The parameters were set for a target performance of 50% with true stimulation provided 50% of the time. The threshold search was defined as complete after 12-16 reversals. Stimulation was applied for 1 sec and repeated upon subject request. Stimulation frequency was held constant at 20 Hz. To prevent overstimulation of sensation, stimulation pulse amplitude (PA) and pulse width (PW) was incremented by 0.1 mA and 10 $\mu s$ steps until the rough threshold was determined. Then PA was held constant at one step (0.1 mA) below the rough threshold while the adaptive staircase method was used to determine a precise PW threshold with 1 $\mu s$ resolution.

Contralateral Pressure Matching

SSO modulation was provided on channel M4. For each trial, the subject was presented with 5 seconds of stimulation, then requested to match the pressure sensation on the contralateral hand by pressing on the manipulator for 5 sec. The last two seconds of the matched pressure data was averaged per trial. The manipulator was shaped to resemble the perceived sensation and was pressed on the same palmar location in the contralateral hand as the perceived sensation. The manipulator was shaped with an approximately ½" diameter circle flat tip with rounded edges out of balsa wood. This manipulator was placed on top of a Flexiforce sensors model A201 (0-1 lb range) manufactured by Tekscan, Inc. (South Boston, Mass.). The sensor was calibrated and the DAQ sampled the sensor at 10 Hz.

Functional Testing

To test the enhancement of control with sensation, the subject plucked the stem off of a cherry with his intact hand while holding the cherry with his prosthetic hand. Pressure measurement on the prosthetic hand was achieved by mounting thin Flexiforce sensors (model A201) on the thumb and index finger tips. Although the subject reported relying on primarily the fingertip pressure sensation for this task, a bend sensor also was mounted to provide prosthesis opening feedback. The sensory feedback stimulation used was SSO with intensity controlled by linear mapping of sensor force to pulse repetition frequency over the range of 10-125 Hz. The test was administered 60 times without providing sensory feedback to the subject. The test was also administered 30 times while providing sensory feedback to the subject. In both cases, half of the tests were administered while the subject could see the cherry being grasped and hear the prosthesis motors and the other half had vision and hearing 100% occluded. The subject wore a sleeping mask for visual blinding and noise-protection ear muffs over ear buds with white noise for audio blinding. After each trial, without providing test results, the subject was asked to rate his confidence in his overall performance.

To evaluate the subject's level of embodiment during functional tasks with sensory feedback, an adapted embodiment questionnaire was given to the subject immediately following functional testing. The questionnaire has 9 statements with which the subject can respond on a −3 to +3 scale from strongly disagree to strongly agree, respectively. Three statements correlate with embodiment, while 6 are control statements for task compliance and suggestibility. The order of statements is randomized. The questionnaire was adapted by changing the phrase "touch of the investigator" to "touch of the objects [manipulated during functional tasks]". Pooled from functional tests on both subjects, "Sensory feedback off" embodiment questionnaire results were compared to the "sensory feedback on" embodiment questionnaire.

Statistical Analysis

Unless otherwise stated, significance was determined with a power of $\alpha=0.05$.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

What is claimed is:

1. A method comprising:
    placing a therapy delivery device in communication with a patient's neural tissue;
    applying a signal to the neural tissue by the therapy delivery device to recruit a population of neural fibers within the neural tissue;
    varying a stimulation parameter of the signal to recruit a different population of neural fibers within the neural tissue that is spatially distinct from the population of neural fibers within the neural tissue in a patterned fashion based on a feedback signal; and
    applying the signal with the varied stimulation parameter to the neural tissue to recruit the different population of neural fibers.

2. The method of claim 1, wherein the stimulation parameter comprises at least one of a stimulation intensity, a stimulation waveform, and an electric field generated by application of the signal.

3. The method of claim 1, wherein the therapy delivery device is an electrode.

4. The method of claim 3, wherein the electrode has multiple active channels.

5. The method of claim 4, wherein the stimulation parameter comprises at least one of a timing and a strength between channels, and
    wherein application of the signal with the varied stimulation parameter alters an electric field generated within the neural tissue.

6. The method of claim 1, wherein the neural tissue comprises at least one of a motor neuron, a sensory neuron, and an autonomic neuron.

7. The method of claim 1, wherein the population of neural fibers and the different population of neural fibers comprise sensory fibers and the signal causes the patient to perceive a sensation.

8. A system comprising:
    a therapy device in communication with a patient's neural tissue to apply a signal to the neural tissue; and
    a stimulator to generate the signal, wherein the signal comprises:
        a first portion to recruit a population of neural fibers within the neural tissue; and
        a second portion with a varied stimulation parameter to recruit a different population of neural fibers within the neural tissue that is spatially distinct from the population of neural fibers within the neural tissue in a patterned fashion, wherein the varied stimulation parameter is varied based on a feedback signal,
    wherein the stimulation parameter is related to an intensity of the signal related to a field generated upon application of the signal.

9. The system of claim 8, wherein the neural tissue comprises at least one of an autonomic neuron, a sensory neuron, and a motor neuron.

10. The system of claim 8, wherein the signal comprises a pattern of a plurality of pulses.

11. The system of claim 10, wherein the parameter related to the intensity is varied for each pulse within the pattern of the plurality of pulses.

12. The system of claim 10, wherein the signal comprises a plurality of patterns, and
    wherein the parameter related to the intensity is varied for each pattern.

13. The system of claim 8, wherein the parameter related to the intensity is varied based on at least one of an input from the neural tissue recorded by a sensor, a user-entered input, and a time.

14. The system of claim 8, wherein the therapy device comprises an electrode.

15. The system of claim 14, wherein the electrode comprises multiple active channels.

16. The system of claim 15, wherein the parameter related to the intensity is related to at least one of a timing and a strength of activation of each of the multiple active channels to change the field generated upon application of the signal.

17. A stimulation device comprising:
- a generator to generate a signal for application to a patient's neural tissue, wherein the signal comprises:
- a first portion to recruit a population of neural fibers within the neural tissue; and
- a second portion with a varied stimulation parameter to recruit a different population of neural fibers within the neural tissue that is spatially distinct from the population of neural fibers within the neural tissue in a patterned fashion;
- a receiver to receive a feedback signal in response to application of the first portion of the signal to the patient's neural tissue,
- wherein the generator varies the stimulation parameter of the second portion of the signal based on the feedback signal.

18. The stimulation device of claim 17, wherein the signal comprises a pattern of pulses.

19. The stimulation device of claim 17, wherein the stimulation parameter is related to an intensity of the second portion of the signal based on the feedback signal.

20. The stimulation device of claim 19, wherein the stimulation parameter is related to at least one of a time or a strength of activation of at least one of a plurality of electrode contacts.

* * * * *